US00PP14179P29

(12) United States Plant Patent
Brown

(10) Patent No.: US PP14,179 P2
(45) Date of Patent: Sep. 30, 2003

(54) PETUNIA PLANT NAMED 'TEDROPUR'

(50) Latin Name: *Petunia x hybrida*
Varietal Denomination: Tedropur

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 0 days.

(21) Appl. No.: 10/259,954

(22) Filed: Sep. 29, 2002

(51) Int. Cl.[7] ..... A01H 5/00
(52) U.S. Cl. ..... Plt./356
(58) Field of Search ..... Plt./356

(56) References Cited

PUBLICATIONS

UPOV ROM GTITM Computer Database, GTI JOUVE Retrieval Software 2002/06, citation(s) for 'Tedropur'.*
http://www.inspection.gc.ca/english/plaveg/pbrpov/cropreport/pet/app00003698e.shtml.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Petunia plant named 'Tedropur', characterized by its compact, outwardly spreading and cascading plant habit; freely branching habit; and numerous small double flowers that are purple-violet in color.

1 Drawing Sheet

CROSS REFERENCE TO RELATED APPLICATIONS

The present application is related to copending U.S. Plant patent application Ser. Nos. 10/259,953 and 10/259,980.

BOTANICAL CLASSIFICATION/CULTIVAR DESIGNATION

Petunia×hybrida cultivar Tedropur.

BACKGROUND OF THE INVENTION

The present Invention relates to a new and distinct cultivar of Petunia plant, botanically known as Petunia×hybrida, and hereinafter referred to by the cultivar name Tedropur.

The new Petunia is a product of a planned breeding program conducted by the Inventor in Cobbitty, New South Wales, Australia. The objective of the breeding program is to create new Petunias with numerous small double flowers with attractive flower colors.

The new Petunia originated from a cross-pollination made by the Inventor in 2000 of a proprietary Petunia selection identified as X99.3, not patented, as the female, or seed parent, with a proprietary Petunia selection identified as code number PKC27, not patented, as the male, or pollen parent. The new Petunia was selected as a single plant from the resulting progeny of the cross-pollination by the Inventor in October, 2000, in a controlled environment in Cobbitty, New South Wales, Australia.

Asexual reproduction of the new cultivar by terminal cuttings taken in a controlled environment in Cobbitty, New South Wales, Australia since October, 2000 has shown that the unique features of this new Petunia are stable and reproduced true to type in successive generations.

SUMMARY OF THE INVENTION

Plants of the cultivar Tedropur have not been observed under all possible environmental conditions. The phenotype may vary somewhat with variations in environment such as temperature and light intensity without, however, any variance in genotype.

The following traits have been repeatedly observed and are determined to be the unique characteristics of 'Tedropur'. These characteristics in combination distinguish 'Tedropur' as a new and distinct Petunia cultivar:

1. Compact, outwardly spreading and cascading plant habit.
2. Freely branching habit.
3. Numerous small double flowers that are purple-violet in color.

Compared to plants of the female parent, the single-flower type selection X99.3, plants of the new Petunia have a more cascading plant habit and darker colored flowers. Plants of the new Petunia differ primarily from plants of the male parent, the double-flower type selection PKC27, in flower color as plants of the male parent have white to blush pink-colored flowers.

Plants of the new Petunia differ primarily from plants of the Petunia cultivars Tedrolip, disclosed in U.S. Plant Patent application Ser. No. 10/259,980, and Tedropi, disclosed in U.S. Plant patent application Ser. No. 10/259,953, in flower coloration.

Plants of the new Petunia can be compared to plants of the cultivar Traveler, disclosed in U.S. Plant patent application Ser. No. 09/450,094 (abandoned). In side-by-side comparisons conducted in Cobbitty, New South Wales, Australia, plants of the new Petunia differed from plants of the cultivar Traveler in the following characteristics:

1. Plants of the new Petunia were more cascading than plants of the cultivar Traveler.
2. Plants of the new Petunia and the cultivar Traveler differed in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical flowering plant of 'Tedropur ' grown in a container.

The photograph at the bottom ofthe sheet comprises a close-up view of typical flowers and leaves of 'Tedropur'.

DETAILED BOTANICAL DESCRIPTION

The aforementioned photographs and following observations and measurements describe plants grown in Encinitas, Calif., in an outdoor nursery during the winter and spring with day temperatures about 24° C., night temperatures about 19° C., and light levels about 4,000 foot-candles. Plants were grown for 19 weeks in one-gallon containers and were pinched one time.

Color references are made to The Royal Horticultural Society Colour Chart, 1995 Edition, except where general terms of ordinary dictionary significance are used.

Botanical classification: Petunia×hybrida cultivar Tedropur.

Parentage:

*Female parent*.—Proprietary Petunia×hybrida selection identified as X99.3, not patented.

*Male parent*.—Proprietary Petunia×hybrida selection identified as PKC27, not patented.

Propagation:

*Type cutting*.—Terminal vegetative cuttings.

*Time to initiate roots*.—About 10 days at 22° C.

*Time to develop roots*.—About 21 days at 22° C.

*Root description*.—Fine, fibrous, white in color.

*Rooting habit*.—Freely branching, dense.

Plant description:

*Form*.—Annual flowering plant; indeterminate; compact; initially upright, then low, outwardly spreading and cascading plant habit; plants eventually becoming hemispherical to spherical in shape. Viscid and glandular pubescent. Moderately vigorous.

*Branching habit*.—Freely branching with more than 75 lateral branches per plant.

*Plant height*.—About 12 cm.

*Plant diameter*.—About 42 cm.

*Lateral branches*.—Length: About 22 cm. Diameter: About 3 mm. Internode length: About 1.2 to 1.5 cm. Texture: Pubescent. Color: 145A.

*Foliage description*.—Arrangement: Before flowering commences: Alternate, simple. After flowering commences: Opposite; simple. Length: About 2.5 cm. Width: About 1.2 cm. Shape: Elliptical. Apex: Broadly acute. Base: Attenuate. Margin: Entire. Texture: Glabrous; glandular. Venation pattern: Pinnate. Color: Young foliage, upper surface: 146A. Young foliage, lower surface: 146B. Mature foliage, upper surface: 147A. Mature foliage, lower surface: 147B. Venation, upper and lower surfaces: 145A. Petiole length: About 9 mm. Petiole diameter: About 2 mm. Petiole color: 144A.

Flower description:

*Flower type and habit*.—Double flowers; flowers face mostly upward or outward; axillary. Flowers persistent. Very freely flowering, about 16 to 20 flowers and flower buds per lateral branch.

*Natural flowering season*.—Long day responsive; spring until frost in the autumn; flowering continuous.

*Flower longevity on the plant*.—About five to ten days.

*Fragrance*.—Not detected.

*Flower size*.—Diameter: About 3.6 cm. Tube length: About 2.4 cm. Throat diameter, distal end: About 1.7 cm. Tube diameter, proximal end: About 4 mm.

*Flower buds* (*showing color*).—Length: About 1.4 cm. Diameter: About 5 mm. Shape: Obovate. Color: More gray than 79B.

*Corolla*.—Quantity/arrangement: About seven fused outer petals, funnelform; interior to outer whorl, about eleven progressively smaller petaloids. Petal length from throat: About 1.5 cm. Petal width: About 1.5 cm. Petal/petaloid shape: Roughly spatulate or fan-shaped. Petal/petaloid apex: Rounded. Petal/petaloid margin: Entire. Petal/petaloid texture: Smooth, velvety. Color: Petal/petaloid, upper surface, when opening: 83C. Petal/petaloid, lower surface, when opening: Lighter than 88D. Petal/petaloid, upper surface, fully opened: 81B; color does not fade with development. Petal/petaloid, lower surface, fully opened: 77C. Flower throat (inside): 79A. Flower tube (outside): 77B to 77C. Venation, upper petal surface: 79A to 79B. Venation, lower petal surface: 79C. Venation, throat: 79A. Venation, tube: 144B.

*Sepals*.—Arrangement/appearance: Single whorl of five sepals fused at base, star-shaped. Length: About 1 cm. Width: About 2.5 mm. Shape: Strap-like; elongate. Apex: Rounded. Margin: Entire. Texture, upper and lower surfaces: Pubescent. Color: Upper surface: 147A. Lower surface: 147B.

*Peduncles*.—Length: About 1.8 cm. Width: About 1 mm. Angle: About 30 to 45° from the stem. Strength: Moderately strong. Texture: Pubescent. Color: 144A.

*Reproductive organs*.—Stamens: None observed, transformed into petaloids. Pistils: Quantity: One per flower. Pistil length: About 4 mm. Stigma shape: Bi-lobed, somewhat asymmetrical. Stigma color: 145A. Style length: About 2 mm. Style color: 145A. Ovary color: 145C.

*Fruit/seed*.—Fruit and seed production has not been observed.

Disease/pest resistance: Plants of the new Petunia have not been noted to be resistant to pathogens or pests common to Petunia.

Temperature tolerance:

Plants of the new Petunia have been observed to tolerate temperatures from 4 to 34° C.

It is claimed:

1. A new and distinct cultivar of Petunia plant named 'Tedropur', as illustrated and described.

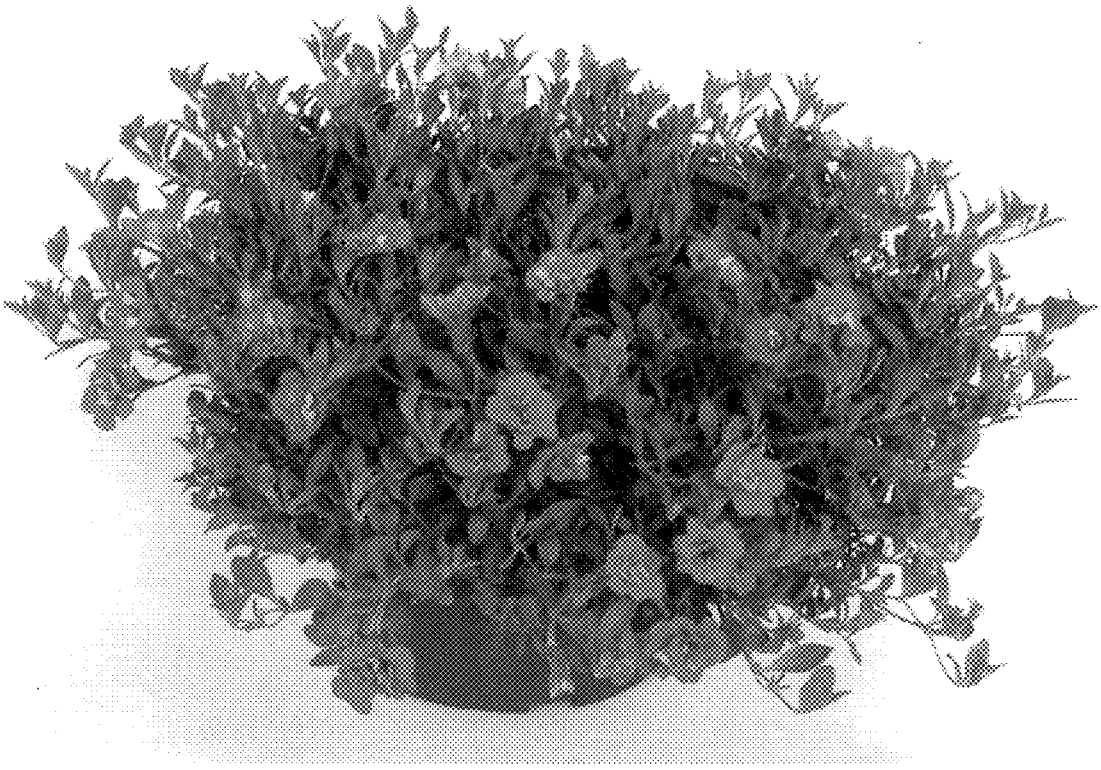
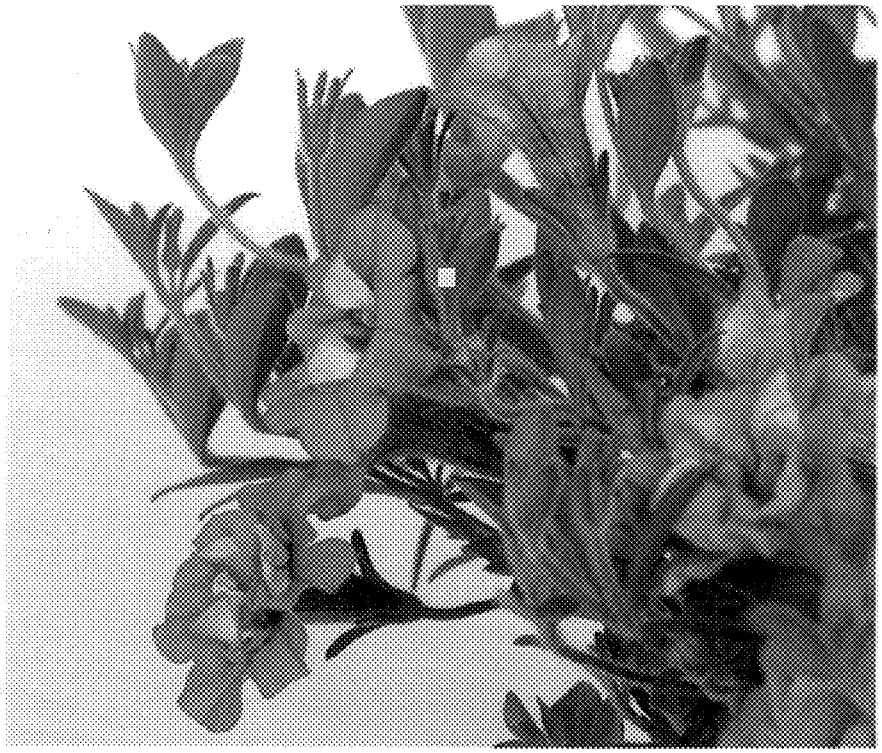

* * * * *